(12) United States Patent
Cartier et al.

(10) Patent No.: US 10,279,082 B2
(45) Date of Patent: May 7, 2019

(54) IMPLANT WITH AN BIOACTIVE COATING AND METHOD FOR PROVIDING THE SAME

(71) Applicant: Biomet Deutschland GmbH, Berlin (DE)

(72) Inventors: Régis Cartier, Berlin (DE); Henrich Mannel, Kleinmachnow (DE); Norbert Baranowski, Mahlow (DE)

(73) Assignee: Biomet Deutschland GmbH, Berlin (DE)

( * ) Notice: Subject to any disclaimer, the term of this patent is extended or adjusted under 35 U.S.C. 154(b) by 1 day.

(21) Appl. No.: 15/745,967

(22) PCT Filed: Jul. 11, 2016

(86) PCT No.: PCT/EP2016/066425
§ 371 (c)(1),
(2) Date: Jan. 18, 2018

(87) PCT Pub. No.: WO2017/012901
PCT Pub. Date: Jan. 26, 2017

(65) Prior Publication Data
US 2018/0207320 A1    Jul. 26, 2018

(30) Foreign Application Priority Data
Jul. 22, 2015   (DE) .......... 10 2015 213 855

(51) Int. Cl.
*A61L 27/54* (2006.01)

(52) U.S. Cl.
CPC ......... *A61L 27/54* (2013.01); *A61L 2300/402* (2013.01); *A61L 2300/406* (2013.01); *A61L 2300/41* (2013.01); *A61L 2300/414* (2013.01); *A61L 2300/416* (2013.01); *A61L 2300/42* (2013.01); *A61L 2300/428* (2013.01); *A61L 2300/43* (2013.01); *A61L 2300/434* (2013.01); *A61L 2300/45* (2013.01); *A61L 2300/608* (2013.01); *A61L 2300/61* (2013.01); *A61L 2400/12* (2013.01); *A61L 2420/02* (2013.01); *A61L 2430/24* (2013.01)

(58) Field of Classification Search
None
See application file for complete search history.

(56) References Cited

U.S. PATENT DOCUMENTS

| | | | |
|---|---|---|---|
| 6,451,373 B1 * | 9/2002 | Hossainy | A61L 27/34 204/192.1 |
| 2006/0171986 A1 | 8/2006 | Kuhn et al. | |
| 2007/0134287 A1 | 6/2007 | Troxel et al. | |

FOREIGN PATENT DOCUMENTS

| | | |
|---|---|---|
| EP | 1683531 B1 | 12/2012 |
| WO | WO-03035123 A1 | 5/2003 |

OTHER PUBLICATIONS

Wu et al. "Drug/device combinations for local drug therapies and infection prophylaxis", Biomaterials 27 (2006) 2450-2467. (Year: 2006).*
Volker et al. "Rifampicin-fosfomycin coating for cementless endoprostheses: Antimicrobial effects against methicillin-sensitive *Staphylococcus aureus* (MSSA) and methicillin-resistant *Staphylococcus aureus* (MRSA)", Acta Biomaterialia 10 (Jun. 2014) 4518-4524. (Year: 2014).*
"German Application Serial No. 102015213855.0 dated Nov. 12, 2015", not in English, 2 pgs.
"International Application Serial No. PCT/EP2016/066425, International Search Report dated Sep. 30, 2016", 3 pgs.
Alt, Volker, et al., "Rifampicin-fosfomycin coating for cementless endoprostheses: Antimicrobial effects against methicillin-sensitive *Staphylococcus aureus* (MSSA) and methicillin-resistant *Staphylococcus aureus* (MRSA)", Acta Biomaterialia vol. 10, issue 10 in Oct. 2014, S. 4518-4524, (2014), 7 pgs.
"International Application Serial No. PCT/EP2016/066425, International Preliminary Report on Patentability dated Feb. 1, 2018", 8 pgs.

* cited by examiner

*Primary Examiner* — Carlos A Azpuru
*Assistant Examiner* — Casey S Hagopian
(74) *Attorney, Agent, or Firm* — Schwegman Lundberg & Woessner, P.A.

(57) ABSTRACT

The present invention relates to an implant having a surface comprising a coating on at least a portion of the surface of the implant, wherein the coating comprises at least two coating layers of bioactive compounds adjacent to each other, obtainable in a process comprising the following steps: providing an implant with a surface, providing a first suspension comprising at least one first bioactive compound in a first solvent, wherein the first bioactive compound is non-soluble or partially soluble in the first solvent, applying said first suspension comprising the at least one first bioactive compound onto at least a part of the implant surface forming a first coating layer; drying the first coating layer, providing a second solution comprising at least one second bioactive compound in a second solvent, wherein the second bioactive compound is soluble or readily soluble in the second solvent; applying said second solution comprising the at least one second bioactive compound onto the first coating layer forming a second coating layer, and drying the second coating layer.

18 Claims, No Drawings

IMPLANT WITH AN BIOACTIVE COATING AND METHOD FOR PROVIDING THE SAME

CLAIM OF PRIORITY

This application is a U.S. national stage application filed under 35 U.S.C. § 371 from International Application Serial No. PCT/EP2016/066425, filed on Jul. 11, 2016, and published as WO 2017/012901 on Jan. 26, 2017, which claims the benefit of priority to Germany Application Serial No. 10 2015 213 855.0, filed on Jul. 22, 2015, which applications and publication are hereby incorporated herein by reference in their entireties.

The present invention relates to an implant having a surface comprising a bioactive coating according to claim 1 and a method for obtaining said implant according to claim 15.

Implants, such as orthopedic implants, are used to replace or repair bone, such as joints (for example knees, hips and elbows). Implants also can be used for stabilizing the skeleton, where it has been destabilized by trauma, such as fractures, or to correct alignments. These implants are made conventionally out of plastics, polymers, ceramics, steel, stainless steel, metals and alloys.

One problem in the clinical application of implants is the mechanic anchoring of the implant in the human body. To promote the anchoring of a prosthesis in the bone, bioactive coatings such as bone-like coatings or peptide coatings such as RGD-coatings are known which promote the ingrowth of the prosthesis or implant into the bone.

However, infections of bone and tissues caused by implants remain another major obstacle. The surface implants provide a platform for bacteria to attach and grow. Due to the rapid growth rate of bacteria they are able to establish infections within days of the surgical procedure which cause a loss of implant fixation, local tissue inflammation and local tissue necrosis and sepsis.

One approach to combat infections is the local employment of antibiotics. This can be done for instance by using local antibiotics carrier such as bone cement, beads, collagen fleeces to which antibiotics are applied to. Said local therapy, however, fails in a significant number often finally leading to the necessity of an amputation.

The most common organisms causing the infectious complications are *Staphylococcus epidermis, Staphylococcus aureus* and different *Pseudomonas* sp., whereby in case of orthopedic procedures *Staphylococcus epidermis* and *Staphylococcus aureus* account for almost 70 to 80% of all infectious organisms.

Another approach for preventing bacterial infections caused by orthopedic procedures is the use of implants coated or surface-treated with antimicrobial agent for inhibiting bacterial attachment and/or inhibiting bacterial growth.

In the past, technologies where developed, which use coating carrier matrices in which an antimicrobial agent such as antibiotics, antiseptics or silver ions are embedded and which are subsequently after implantation delivered to the implant surface. Such a carrier matrix comprises for instance polymer or polymer layers made of non-absorbable polymer and/or bio absorbable polymer. These polymers can be selected from a group of polylactides, polyacrylates, polysiloxanes, polyurethanes, chitosan, dextrin, cyclodextrin, polyacrylamide, polystyrenes, polyvinylpyrollidon, glycoseaminglycanes, polyethylenglycole and others.

It is also known to use a calcium phosphate coated metal implant as a repository for the bioactive agent (WO 03/035123). Here the implant is at first coated with one or more layers of calcium phosphate minerals such as hydroxyapatite. The bioactive agent is applied to the implant only immediately before implantation.

EP 1 683 531 B1 discloses an antibiotic coating of an implant consisting of a matrix made of fatty acid or fatty acid esters such as palmitate, Cetylpalmitate, Glycerinstearate and others. The antibiotic is suspended in said matrix.

Another approach for providing an implant stabile coated with a bioactive agent is the addition of fibers to the coating for providing a fiber reinforcement. Such fibers can have length of up to 5 µm.

The approaches for providing coated implants known so far have several drawbacks for one or more reasons. For instance, when using a coating comprising an antimicrobial agent embedded in a polymer the amount of antimicrobial agent being released into the tissue after implantation is limited and thus an effective prevention of bacterial infection cannot be guaranteed. Furthermore, a lot of the polymers as applied in the past may be degraded and release monomers which may cause other health complications. Furthermore, the use of carriers should be avoided since the transfer of shear forces takes place via an intermediate layer reducing the primary stability. Also, the application of an antimicrobial coating by the manufacturer add extremely high costs to the implant. As a result, only a few precoated devices are commercially available. A further problem is the stability of a coating which can reduce the shelf life of the coated implant tremendously.

Accordingly, there is still a need for providing implants with an antimicrobial coating for treating and preventing bacterial infections, which can be produced at reasonable costs and which also are characterized by a reasonable shelf life. Also, there is a need for an implant which does not hamper the bone healing and does not have any negative effect on the implant-bone interface.

This object is achieved by an implant having a surface comprising a coating according to claim 1 and a method for obtaining such an implant according to claim 15.

Accordingly, an implant having a surface is provided, wherein the implant comprises a coating on at least a portion of the surface of the implant, wherein the coating comprises at least two coating layers of bioactive compounds adjacent to each other.

According to the invention the present implant is obtainable in a process comprising the following steps:

providing an implant with a surface, providing a first suspension comprising at least one first bioactive compound in a first solvent, wherein the first bioactive compound is non-soluble or only partially soluble in the first solvent, applying said first suspension comprising the at least one first bioactive compound onto at least a part of the implant surface forming a first coating layer;

drying the first coating layer, providing a second solution comprising at least one second bioactive compound in a second solvent, wherein the second bioactive compound is soluble or readily soluble in the second solvent;

applying said second solution comprising the at least one second bioactive compound onto the first coating layer forming a second coating layer, and drying the second coating layer.

Accordingly, the at least two layers of bioactive compounds are applied in an iterative process wherein in a first step the at least one first bioactive compound is applied to the implant surface, in particular metallic implant surface, and after intermediate drying the first coating layer the at least one second bioactive compound is applied onto the first coating layer. Thus, the layers comprising the at least one first and at least one second bioactive compound may form separate layers or may also form at least partially overlapping layers The coating can also be described such that the outer (second) layer conceals the inner (first) layer on the implant surface.

It was surprisingly found when applying such an iterative process of applying at least two bioactive compounds to an implant surface that the coating adheres to the implant very well and a stable coating layer comprising at least two bioactive compounds is formed. The improved adherence of the coating is shown in abrasion tests as described in the Examples.

This is in particular remarkable in those cases wherein one bioactive compound, such as the at least one bioactive compound forming the first coating layer has a low solubility in typically used organic solvents such as lower organic alcohols and/or water.

In this case the first bioactive compound is applied to the implant surface using a suspension, i.e. the first bioactive compound is dissolved only to a limited extent in the solvent used such that a solid rather than a liquid is applied to the implant surface.

For example the first bioactive compound is practically insoluble in the common organic solvents such as tetrahydrofuran (THF), dimethylsulfoxide (DMSO), methanol, ethanol, or isopropanol.

Even in an aqueous solution with an organic solvent, such as an alcohol the solubility is limited. In such cases the solubility of the first bioactive compound in a aqueous solution is lower than 1 mg/ml, preferably lower than 0.8 mg/ml, in particular preferably lower than 0.5 mg/ml. For example, the solubility of the first bioactive compound in a water/isopropanol mixture is very low (e.g. solubility in isopropanol/water 2:1 V/V is less than 0.8 mg/ml).

The solubility of the first bioactive compound in water may be less than 5 mg/ml, preferably less than 4 mg/ml, in particular less than 3 mg/ml. However, the use of water as only solvent for the first bioactive compound is not preferred since the drying process would be prolonged and hampered.

Furthermore, the particle size of the first bioactive compound in the suspension is preferably smaller than 15 μm, preferably smaller than 10 μm, most preferably smaller than 5 μm. Such as suspension may be obtained using high pressure homogenizer.

In the result the first bioactive compound forms (after drying) a flaky, powder-like coating on the implant surface which can be rather easily rubbed off. The first coating layer can also be described as a patch-like powder coating; i.e. a non-continuous coating layer.

The second coating layer comprising the at least one second bioactive compound which is soluble in the second solvent forms in contrast an almost continuous coating layer; i.e. continuous coating surface. The second coating layer conceals or agglutinates the first layer on the implant surface.

The solvent or suspension means for the suspension of the first bioactive compound forming the first coating layer may be selected from non-polar solvents such as alkanes, alkenes, ether, carboxylic ester, polar solvents such as water or organic alcohols or mixtures thereof. In particular preferred are methanol, ethanol, n-propanol, iso-propanol, a butanol, water or a mixture thereof.

The choice of the appropriate solvent for the at least one first bioactive compound (and possible further ones) for forming the first layer depends on the overall solubility of said compound. The first coating layer is formed in particular by a one or more bioactive compounds which have a general low solubility in any of the solvents compatible to the human organism. As stated above the minimum solubility of the first bioactive compound forming the first coating layer is such that the particle size of the first bioactive compound in the suspension is smaller than 15 μm.

The second coating layer comprising the at least one second bioactive compound which is soluble, preferably completely soluble in the second solvent, forms in contrast a continuous coating layer; i.e. continuous coating surface. The second coating layer conceals or agglutinates the combination of first and second layer on the implant surface.

The solvent for the solution of the second bioactive compound forming the second coating layer may be a polar solvent such as an organic alcohol or water. In a preferred embodiment the solvent of the second bioactive compound is methanol, ethanol, n-propanol, iso-propanol, a butanol, water or a mixture thereof.

In a particular preferred embodiment of the present implant the coating does not comprise any additional compounds for promoting adhesion of the coating to the implant surface and which may form a carrier matrix or support matrix. Thus, the bioactive compounds used in any of the at least two layers are not incorporated into any polymer, polymer layer or calcium phosphate layer. Furthermore, each of the coating layers does not contain any reinforcing material such as fibers or any other adhesive aid such as a waxy material which may be a lipid selected from the group consisting of fatty acids, triacylglycerols, diacylglycerols, glycerophospholipids, phospatidylcholine and mixtures thereof. Furthermore, the bioactive coating of the present implant does not comprise any enzymes or enzymatically degradable linkages. Thus, the bioactive coating of the present implant does not comprise or contain any additional substrate which could promote adhesion to the implant surface. The only components included in the coating layers may be an antioxidative agent for anti aging reasons.

In a variant of the present implant the first coating layer comprises more than one bioactive compound, in particular two or three bioactive compounds.

In a further embodiment of the present implant the first and second bioactive compounds are selected from a group consisting of pain reliever, blood thinning substances (anticoagulant), hormones, cytostatic substances, growth factors, inflammation inhibitors and antibiotics.

Pain relievers may be selected from a group comprising bupivacain, ibuprofen, paracetamol, opiate and lidocain.

Blood thinning substances may be selected from a group comprising heparins or coumarines Suitable hormones used as coating material may be estrogens and gestagens.

Cytostatic substances are preferably methotrexat (MTX), anthracycline such as doxorubicin, daunorubicin or idarubicin, cisplatin, taxane or topoisomerase-inhibitors such as toptecan. Growth factors are preferably selected from the FGF-family (Fibroblast Growth Factor); TGF-family (Transforming growth factor), Hedgehog, Wingless, Delta and Serrate, and Ephrines. The preferred growth factors are Fibroblast growth factor (FGF), Transforming growth factor (TGF), Platelet Derived Growth Factor (PDGF), Epidermal Growth Factor (EGF), Granulocyte-Macrophage Colony Stimulating Factor (GMCSF), Vascular Endothelial Growth Factor (VEGF), Insulin-like Growth Factors (IGF), Hepatocyte Growth Factor (HGF), Interleukin-1B, -8 (IL-1B, IL-8), Nerve Growth Factor (NGF). The most preferred growth factors are BMP-2, BMP-5 and BMP-7.

Inflammation inhibitors are selected from a groups comprising non-steroidal antiphlogistic such as Ibuprofen, Acetyl salicylic acid, Diclofenac, Indometacin or Phenylbutazon, or steroidal antiphlogistics such as Dexamethason, Hydrocortison or Prednisolon.

In an embodiment of the present implant the at least one first layer which is adjacent to the surface of the implant comprises at least one antibiotic selected from the group of antibiotics effecting the bacterial cell wall or its synthesis. In an embodiment, said antibiotics working as inhibitor of bacterial cell wall synthesis or destabilizing and rupturing the cell wall directly comprise glycopeptides, fosfomycin and polypeptides. In an embodiment the glycopeptides chosen are vancomycin and teicoplanin. The polypeptides chosen are bacitracin and daptomycin. The most preferred antibiotic used as the first coating layer adjacent to the implant surface is fosfomycin.

The first antibiotic containing layer is thereby directly coated on the implant surface that means that no auxiliary agent for promoting the adhesion of the antibiotic to the implant surface is used. However, before applying the first coating layer the implant surface may be pre-treated such as sand blasted or glass bead blasted.

In a further embodiment of the present implant the second layer comprising an antibiotic arranged on the first layer comprises at least one antibiotic selected from a group of bacterial RNA polymerase inhibitors. In particular, the antibiotic of the second coating layer is selected from a group comprising ansamycins, in particular rifamycins. Particularly, rifampicin, rifampin, rifabutin, rifapentine or rifaximin may be chosen. A second coating layer containing a rifamycin, in particular rifampicin is particularly suited in eliminating intracellular staphylococci, which have been previously shown to be reduced within three days after local administration of a pharmaceutical composition comprising rifampin.

In a most preferred embodiment of the present implant the first coating layer adjacent to the implant surface comprises fosfomycin and the second coating layer arranged on the first coating layer comprises a rifamycin. The coating of the present implant comprising a rifamycin and fosfomycin covers essentially the entire germ spectrum to be reduced and eradicated and is thus also effective against problematic bacteria like MRSA and MRSE. Fosfomycin has the further property that it binds reversibly to hydroxyapatite and thus remains even after release from the implant longer in a bone than any other antibiotic. Fosfomycin has the further advantage that it is a small molecule able to diffuse through the bone tissue.

It is to be understood within the frame of the present invention that the antibiotics described herein can also be used in form of their pharmaceutical acceptable salts or derivatives thereof.

In another embodiment, the present implant is selected from a group comprising an implantable prosthesis, in particular a hip prosthesis, a shoulder prosthesis, an elbow prosthesis, a knee prosthesis or a vertebral implant or an implant for trauma surgery such as screws, plates etc.

In another embodiment of the present implant, the concentration of the bioactive compound, in particular antibiotic concentration, in the first coating layer which is directly adjacent to the implant surface is between 50 and 500 $\mu g/cm^2$ surface area, preferably between 70 and 350 $\mu g/cm^2$, in particular preferably between 150 and 250 $\mu g/cm^2$. In a most preferred embodiment, the concentration of the bioactive compound in the first coating layer is 300 $\mu g/cm^2$.

In a further embodiment, the concentration of the bioactive compound, in particular the antibiotic concentration, in the second coating layer arranged on the first coating layer is between 30 and 350 $\mu g/cm^2$ surface area, preferably between 50 and 250 $\mu g/cm^2$, in particular preferably between 50 and 100 $\mu g/cm^2$. The most preferred antibiotic concentration in the second coating layer is 60 $\mu g/cm^2$.

In a further embodiment the present implant comprises at least one antioxidative agent in at least one of the coating layers, in particular the second coating layer. Preferably, the first coating layer adjacent to the implant surface does not contain any antioxidative agent, wherein the second layer arranged on the first layer contains the antioxidative agent.

The use of an antioxidative agent in at least one of the coating layers comprising a bioactive compound, in particular an antibiotic, on the implant improves the stability of the bioactive compound. Thus, the shelf life of the coated implant is increased.

The at least one antioxidative agent is thereby selected preferably from a group comprising vitamin C, Vitamin E, polyphenol-containing compositions and others. The polyphenol-containing compositions comprise preferably flavonoids, benzoic acid derivatives such as hydroxybenzoic acids like vanillic acid, tri-hydroxybenzoic acid such as gallic acid and dihydroxybenzoic acid such as protocatechuic acid, cinnamon acid derivatives such as p-coumaric acid and stilbene derivatives such as Resveratrol.

It is in particular preferred if the antioxidative agent is part of the second coating layer, i.e. the second coating layer comprises a mixture of an antibiotic and an antioxidative agent.

The concentration of the antioxidative agent in the second coating layer may be 10 to 50%, preferably 15 to 40%, in particular preferably 20 to 30% of the weight of the second bioactive compound. For example in case 1 g of the second bioactive compound is used than the solution may be supplemented with 200 mg of an antioxidative agent such as Vitamin C.

In a most preferred embodiment, the implant according to the invention comprises a first coating layer comprising fosfomycin, and a second coating layer comprising a rifamycin, in particular rifampicin, mixed with an antioxidative agent, in particular vitamin C. It is preferred that the first coating layer comprises 300 $\mu g/cm^2$ per surface area fosfomycin and 60 $\mu g/cm^2$ per surface area rifamycin and preferably 12 $\mu g/cm^2$ Vitamin C. The present implant is further used for treating a tissue infection of the subject into which the implant is implanted, wherein the tissue may be for example soft tissue and/or bone tissue and/or bone. These infections might occur due to a surgical operation, particularly due to an operation related to implanting the implant into a human or non-human body. Thus, the treatment might be applied to a human or non-human body.

In an embodiment, the infected tissue to be treated is acutely or chronically infected. A combination of an acute and a chronic infection, i.e., the acute infection overlying the chronic infection, might also be treated.

In a further embodiment, the infected cells, such as infected tissue cells, are osteoplasts, leucocytes, erythrocytes, keratinocytes, fibroblasts, fat cells, muscle cells and/or endothelial cells.

The microbial infection to be treated by using the present implant is caused by a gram-negative and/or gram-positive bacteria or yeasts. Such organisms include *Klebsiella*, *Enterobacter*, *Acinetobacter*, *Pseudomonas*, *Escherichia*, and *Staphylococcus*. Specific bacteria include *Staphylococcus aureus*, as represented by strain NCTC 8325 and methicillin resistant strains which presently cause significant problems in hospital environments. Further targets are *Staphylococcus epidermidis*, represented by strain NCTC 11047, and yeasts such as Candida albicans, represented by strain ATCC 26555. The treatment of infections caused by the gram-positive staphylococci type, in particular by *Staphylococcus aureus* and/or *Staphylococcus epidermidis*, is mostly preferred.

The first and second coating layer are preferably applied to the implant surface using at least one first and at least one second ink jet, respectively, or only one ink jet for both layers. Thus, the coating layers of the present implant are applied using ink jets, which apply droplets of the coating substance (here the antibiotic suspensions or solutions) onto the implant surface.

In a preferred embodiment, the implant to be coated undergoes a special pre-treatment before applying the coating, in particular the implant surface is sand blasted or glass bead blasted. The surface treatment improved the adhesion of the first coating layer to the implant surface. However, the coating process can also be conducted on non-treated surfaces or machined surfaces.

As mentioned previously, the at least one first suspension comprises the at least one first bioactive compound, such as an antibiotic, in a particle size of smaller than 15 µm, preferably smaller 10 µm, in particular preferably smaller than 5 µm.

In order to obtain such solution or suspension, the first bioactive compound such as the first antibiotic is preferably homogenized in an appropriate suspension means or solvent until the defined particle size and concentration is obtained. Such a homogenization can be for instance conducted in a high pressure homogenizer. During or after applying the first suspension onto the implant surface using the first ink jet the solvent or suspension means evaporates and thereby a first coating layer is obtained.

It is in particular preferred if a suspension of fosfomycin-calcium-monohydrate in 2-propanol/water (2:1 volume/volume) is provided and is homogenized in a high pressure homogenizer until 80% of the fosfomycin particles have a particle diameter or particle size of less than 10 µm.

It is also preferred, if rifampicin as the second antibiotic is provided in a mixture with vitamin c and methanol, which is subsequently applied to the first fosfomycin layer using a second ink jet.

Further details of the invention are explained in the following with reference to exemplary embodiments.

EXAMPLE 1

A suspension of fosfomycin-calcium-monohydrate in 2-propanol/water=2:1 Vol/Vol is provided and is homogenized in an appropriate high pressure homogenizer. The concentration of the fosfoymicin salt in the suspension is such that after application onto the implant surface a fosfomycin concentration in the coating layer is 300 µg/cm² per implant surface area is defined.

The fosfomycin suspension contains 80% of particles, which have a diameter less than 10 µm. Such a fosfomycin suspension is stable for about 35 days. The fosfomycin suspension is subsequently applied to the implant surface using a first ink jet.

In parallel, a second solution comprising the second antibiotic for the second coating layer is provided by dissolving rifampicin and vitamin C in methanol. The rifampicin concentration in the solution is chosen such that the final rifampicin concentration on the implant is 60 µg/cm².

Said second solution comprising rifampicin and vitamin C is subsequently coated onto the first fosfomycin coating layer using a second separated ink jet.

EXAMPLE 2

The adherence of the fosfomycin-rifampicin double coating layer was determined applying a wiping test. A substrate, here a glass substrate, was coated at first with a fosfomycin-Ca monohydrate suspension. Subsequently, a part of the glass substrate coated with fosfomycin-Ca was partially coated with rifampicin.

The fosfomycin-Ca particles are distributed over the surface with a density of about 430 µg/cm² (corresponding to about 300 µg/cm² active fosfomycin). The density of rifampicin applied to the fosfomycin-Ca layer is about 60 µg/cm².

The completely coated substrate was then wiped using a polyester cloth. By doing so in areas where only fosfomycin-Ca was applied (i.e. without a second layer of rifampicin) the fosfomycin-Ca was largely removed. In contrast, those areas, where the fosfomycin was coated with rifampicin, stayed intact. Thus, the application of a second layer of rifampicin prevented a removal of the first fosfomycin layer.

EXAMPLE 3

A suspension of Dexamethason in water/ethanol was prepared in a high pressure homogenizer. The suspension was applied to an implant surface using a first ink jet. The first coating layer is dried.

In parallel a methanol solution of Lidocain(hydrochlorid) was provided and applied to the first layer using a second ink jet.

The invention claimed is:

1. An implant having a surface comprising a coating on at least a portion of the surface of the implant, wherein the coating comprises at least two coating layers of bioactive compounds adjacent to each other, wherein the first coating layer is a patch-like, non-continuous powder coating layer, and the second coating layer is a continuous coating layer concealing or agglutinating the first coating layer, the implant obtainable in a process comprising the steps of:
    providing an implant with a surface;
    providing a first suspension comprising at least one first bioactive compound in a first solvent, wherein the first bioactive compound is non-soluble or partially soluble in the first solvent;
    applying said first suspension comprising the at least one first bioactive compound onto at least a part of the implant surface forming a first coating layer;
    drying the first coating layer;
    providing a second solution comprising at least one second bioactive compound in a second solvent, wherein the second bioactive compound is soluble or readily soluble in the second solvent;
    applying said second solution comprising the at least one second bioactive compound onto the first coating layer forming a second coating layer; and
    drying the second coating layer.

2. The implant according to claim 1, wherein the first and second bioactive compounds are selected from the group consisting of antibiotics, pain reliever, anti-coagulation substances, heparins, hormones, cytostatic substances, growth factors and inflammation inhibitors.

3. The implant according to claim 1, wherein the first coating layer comprises more than one bioactive compound.

4. The implant according to claim 1, wherein the at least one first coating layer which is adjacent to the surface of the implant comprises at least one antibiotic that affects the bacterial cell wall or its synthesis.

5. The implant according to claim 4, wherein the at least one antibiotic is selected from the group consisting of glycopeptides, fosfomycin and polypeptides.

6. The implant according to claim 1, wherein the second coating layer arranged on the first coating layer comprises at least one antibiotic, wherein the at least one antibiotic comprises a bacterial RNA polymerase inhibitor.

7. The implant according to claim 6, wherein the antibiotic comprises a rifamycin.

8. The implant according to claim 1, wherein the first coating layer adjacent to the implant surface comprises fosfomycin and the second coating layer arranged on the first layer comprises a rifamycin.

9. The implant according to claim 1, wherein the concentration of the bioactive compound in the first coating layer adjacent to the implant surface is between 50 and 500 µg/cm$^2$.

10. The implant according to claim 9, wherein the concentration of the bioactive compound in the second coating layer arranged on the first coating layer is between 30 and 350 µg/cm$^2$.

11. The implant according to claim 1, wherein at least one of the coating layers comprises at least one antioxidative agent.

12. The implant according to claim 1, wherein the implant is a hip prosthesis, a shoulder prosthesis, an elbow prosthesis, a knee prosthesis or a vertebral implant or an implant for trauma surgery.

13. The implant according to claim 1, wherein the implant surface is pre-treated before applying the coating by sand blasting or glass bead blasting.

14. A method for obtaining an implant comprising:
providing an implant with a surface;
providing a first suspension comprising at least one first bioactive compound in a first solvent, wherein the first bioactive compound is non-soluble in the first solvent;
applying said first suspension comprising the at least one first bioactive compound onto at least a part of the implant surface forming a first coating layer;
drying the first coating layer, resulting in a first patch-like, non-continuous coating layer;
providing a second solution comprising at least one second bioactive compound in a second solvent, wherein the second bioactive compound is soluble in the second solvent;
applying said second solution comprising the at least one second bioactive compound onto the first coating layer forming a second coating layer; and
drying the second coating layer, resulting in a continuous coating layer concealing or agglutinating the first coating layer.

15. The implant according to claim 5, wherein the at least one antibiotic is vancomycin or teicoplanin.

16. The implant according to claim 5, wherein the at least one antibiotic is bacitracin or daptomycin.

17. The method according to claim 14, wherein said first suspension is applied using at least one first ink jet.

18. The method according to claim 14, wherein said second solution is applied using at least one second ink jet.

* * * * *